(12) United States Patent
Ambery et al.

(10) Patent No.: US 10,112,946 B2
(45) Date of Patent: Oct. 30, 2018

(54) COMPOSITION

(75) Inventors: Claire Louise Ambery, Middlesex (GB); Christopher David Edwards, Stevenage (GB)

(73) Assignee: GlaxoSmithKline LLC, Wilmington, DE (US)

( * ) Notice: Subject to any disclaimer, the term of this patent is extended or adjusted under 35 U.S.C. 154(b) by 589 days.

(21) Appl. No.: 14/234,070

(22) PCT Filed: Jul. 19, 2012

(86) PCT No.: PCT/EP2012/064139
§ 371 (c)(1),
(2), (4) Date: May 13, 2014

(87) PCT Pub. No.: WO2013/014052
PCT Pub. Date: Jan. 31, 2013

(65) Prior Publication Data
US 2014/0288099 A1    Sep. 25, 2014

Related U.S. Application Data

(60) Provisional application No. 61/510,624, filed on Jul. 22, 2011.

(51) Int. Cl.
*C07D 473/28* (2006.01)
*A61K 9/00* (2006.01)
*A61K 9/12* (2006.01)
*A61K 31/522* (2006.01)

(52) U.S. Cl.
CPC .......... *C07D 473/28* (2013.01); *A61K 9/0043* (2013.01); *A61K 9/12* (2013.01); *A61K 31/522* (2013.01); *A61K 9/0073* (2013.01)

(58) Field of Classification Search
CPC .................................................. C07D 473/28
USPC ....................................................... 514/263.2
See application file for complete search history.

(56) References Cited

U.S. PATENT DOCUMENTS

| | | | |
|---|---|---|---|
| 5,962,479 A | 10/1999 | Chen | |
| 6,376,501 B1 | 4/2002 | Isobe et al. | |
| 6,552,192 B1 | 4/2003 | Hanuset et al. | |
| 7,125,880 B1 | 10/2006 | Chen | |
| 7,390,890 B2 | 6/2008 | Furneaux et al. | |
| 7,642,350 B2 | 1/2010 | Pryde | |
| 7,977,344 B2 | 7/2011 | Lazarides et al. | |
| 8,067,413 B2 | 11/2011 | Bonnert et al. | |
| 8,067,426 B2 | 11/2011 | Biggadike et al. | |
| 8,563,717 B2 | 10/2013 | Bazin-Lee et al. | |
| 8,575,181 B2 | 11/2013 | Campos et al. | |
| 8,575,340 B2 | 11/2013 | Bazin-Lee et al. | |
| 8,703,754 B2 | 4/2014 | Gibbon et al. | |
| 8,765,772 B2 | 7/2014 | Biggadike et al. | |
| 8,802,684 B2 | 8/2014 | Bazin-Lee et al. | |
| 9,173,872 B2 | 11/2015 | Coe et al. | |
| 9,233,962 B2 | 1/2016 | Biggadike et al. | |
| 9,346,806 B2 | 5/2016 | Biggadike et al. | |
| 9,877,968 B2 | 1/2018 | Biggadike et al. | |
| 2001/0020030 A1 | 9/2001 | Stewart et al. | |
| 2002/0037886 A1 | 3/2002 | Andersson et al. | |
| 2003/0187261 A1 | 10/2003 | Havlicek et al. | |
| 2003/0191086 A1 | 10/2003 | Hanus et al. | |
| 2003/0220365 A1 | 11/2003 | Stewart et al. | |
| 2003/0236216 A1 | 12/2003 | Devos et al. | |

(Continued)

FOREIGN PATENT DOCUMENTS

| EP | 0773023 A1 | 5/1997 |
|---|---|---|
| EP | 1043021 A1 | 7/1999 |

(Continued)

OTHER PUBLICATIONS

Akira, S., Toll-like receptors: critical proteins linking innate and acquired immunity, Nat. Immuno. 2001; 2(8); 675-680.
Allergic Rhinitis—Prevention (http://www.webmd.com/allergies/tc/allergic-rhinitis-prevention); WebMD: Allergic Health Center; Jun. 30, 2011.
Asthma Prevention (http://www.webmd.com/asthma/guide/asthma-prevention); WebMD: Asthma Health Center; May 13, 2012.
Berge, S.M., et al. J. Pharmaceutical Science, Published 1977, vol. 66, pp. 1-19.
Borden E.C., et al., Interferons at age 50: past, current and future impact on biomedicine. Nat Rev Drug Discov., Dec. 2007, 6(12), 975-990.

(Continued)

*Primary Examiner* — Melenie L McCormick
*Assistant Examiner* — Taina D Matos Negron
(74) *Attorney, Agent, or Firm* — Leah M. Octavio; Fang Qian

(57) ABSTRACT

Compound (I), and pharmaceutically acceptable salts thereof, are inducers of human interferon. Certain discrete and particular dosages of Compound (I) may be particularly useful in the treatment of various disorders, for example the treatment of allergic diseases and other inflammatory conditions, for example allergic rhinitis and allergic asthma.

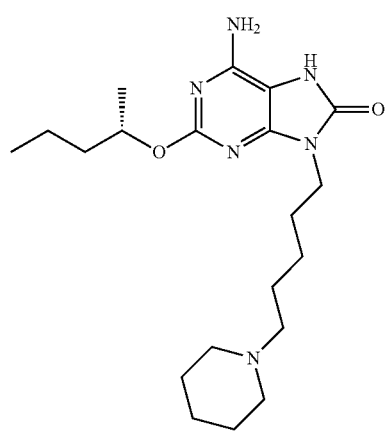

Compound (I)

2 Claims, 3 Drawing Sheets

(56) References Cited

U.S. PATENT DOCUMENTS

| | | |
|---|---|---|
| 2004/0029054 A1 | 2/2004 | Vaeth et al. |
| 2004/0063658 A1 | 4/2004 | Roberts et al. |
| 2005/0054590 A1 | 3/2005 | Averett |
| 2006/0029642 A1 | 2/2006 | Miljkovic et al. |
| 2006/0052403 A1 | 3/2006 | Isobe et al. |
| 2006/0148805 A1 | 7/2006 | Chen et al. |
| 2006/0264448 A1 | 11/2006 | Pryde |
| 2007/0190071 A1 | 8/2007 | Kurimoto et al. |
| 2007/0197478 A1 | 8/2007 | Jones et al. |
| 2007/0225303 A1 | 9/2007 | Ogita et al. |
| 2007/0275984 A1 | 11/2007 | Imogai et al. |
| 2008/0008682 A1 | 1/2008 | Chong et al. |
| 2008/0269240 A1 | 10/2008 | Hashimoto et al. |
| 2008/0300244 A1 | 12/2008 | Bonnert et al. |
| 2009/0047249 A1 | 2/2009 | Graupe et al. |
| 2009/0082332 A1 | 3/2009 | Abbot et al. |
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0131458 A1 | 5/2009 | Lazarides et al. |
| 2009/0143400 A1 | 6/2009 | McInally et al. |
| 2009/0192153 A1 | 7/2009 | Hashimoto et al. |
| 2009/0202484 A1 | 8/2009 | Chong et al. |
| 2009/0233948 A1 | 9/2009 | Evans et al. |
| 2009/0324551 A1 | 12/2009 | Carson et al. |
| 2009/0325877 A1 | 12/2009 | Grunt et al. |
| 2010/0010016 A1 | 1/2010 | Gangjee |
| 2010/0075995 A1 | 3/2010 | Biggadike et al. |
| 2010/0087443 A1 | 4/2010 | Bonnert et al. |
| 2010/0093998 A1 | 4/2010 | Isobe et al. |
| 2010/0099870 A1 | 4/2010 | Isobe et al. |
| 2010/0120799 A1 | 5/2010 | Lazarides et al. |
| 2010/0130491 A1 | 5/2010 | Bonnert et al. |
| 2010/0240623 A1 | 9/2010 | Cook et al. |
| 2011/0135671 A1 | 6/2011 | Bazin-Lee et al. |
| 2011/0229500 A1 | 9/2011 | Bigoadike et al. |
| 2011/0269781 A1 | 11/2011 | Lazarides et al. |
| 2012/0035193 A1 | 2/2012 | Biggadike et al. |
| 2012/0135963 A1 | 5/2012 | Johnson |
| 2012/0171229 A1 | 7/2012 | Zepp et al. |
| 2012/0264768 A1 | 10/2012 | Gangee |
| 2012/0283438 A1 | 11/2012 | Lazarides et al. |
| 2012/0315291 A1 | 12/2012 | Basin-Lee et al. |
| 2014/0056928 A1 | 2/2014 | Coe et al. |
| 2014/0288099 A1 | 9/2014 | Ambery et al. |
| 2014/0336175 A1 | 11/2014 | Biggadike et al. |
| 2015/0225403 A1 | 8/2015 | Coe et al. |

FOREIGN PATENT DOCUMENTS

| | | |
|---|---|---|
| EP | 1348707 A1 | 10/2003 |
| EP | 1939198 A1 | 3/2007 |
| EP | 1939199 A1 | 7/2008 |
| EP | 2138497 A1 | 12/2009 |
| RU | 2221799 C2 | 1/2004 |
| WO | 9533750 A1 | 12/1995 |
| WO | 9749706 A1 | 12/1997 |
| WO | 1999040091 A1 | 8/1999 |
| WO | 0043394 A1 | 7/2000 |
| WO | 0149688 A1 | 7/2001 |
| WO | 2001083472 A1 | 11/2001 |
| WO | 2003053970 A1 | 7/2003 |
| WO | 2004018496 A1 | 3/2004 |
| WO | 2004029054 A1 | 4/2004 |
| WO | 2005002520 A2 | 1/2005 |
| WO | 2011017611 A1 | 2/2005 |
| WO | 2005020892 A2 | 3/2005 |
| WO | 2005025583 A2 | 3/2005 |
| WO | 2005079195 A2 | 9/2005 |
| WO | 2005097800 A1 | 10/2005 |
| WO | 2005110410 A2 | 11/2005 |
| WO | 2006030031 A1 | 3/2006 |
| WO | 2006117670 A1 | 11/2006 |
| WO | 2007013964 A1 | 2/2007 |
| WO | 2007024944 A1 | 3/2007 |
| WO | 2007028129 A1 | 3/2007 |
| WO | 2007034881 A1 | 3/2007 |
| WO | 2007041863 A1 | 4/2007 |
| WO | 2007093901 A1 | 8/2007 |
| WO | 2007110868 A1 | 10/2007 |
| WO | 2007142755 A2 | 12/2007 |
| WO | 20070138084 A2 | 12/2007 |
| WO | 2008004948 A1 | 1/2008 |
| WO | 2008100457 A2 | 8/2008 |
| WO | 2008101867 A1 | 8/2008 |
| WO | 2008114008 A1 | 9/2008 |
| WO | 2008154221 A2 | 12/2008 |
| WO | 2009019505 A1 | 2/2009 |
| WO | 2009023179 A2 | 2/2009 |
| WO | 2009078798 A1 | 6/2009 |
| WO | 2010006025 A1 | 1/2010 |
| WO | 2010018130 A1 | 2/2010 |
| WO | 2010018131 A1 | 2/2010 |
| WO | 2010018132 A1 | 2/2010 |
| WO | 2010018134 A1 | 2/2010 |
| WO | 20100018133 A1 | 2/2010 |
| WO | WO2010018133 * | 2/2010 |
| WO | 2010083725 A1 | 7/2010 |
| WO | 2011098451 A1 | 8/2011 |
| WO | 20110098452 A1 | 8/2011 |
| WO | 2012009258 A2 | 1/2012 |
| WO | 2012106343 A2 | 8/2012 |
| WO | 2014081643 A1 | 5/2014 |
| WO | 2014081644 A1 | 5/2014 |
| WO | 2014081645 A1 | 5/2014 |
| WO | 2015124591 A1 | 8/2015 |

OTHER PUBLICATIONS

Czarniecki, M. Small Molecule Modulators of Toll-like Receptors, Nov. 13, 2008, vol. 51(21), 6621-6626.

Corren, J., et al.; A Randomized, Controlled, Phase 2 Study of AMG 317, an IL-4Rα Antagonist, in Patients with Asthma; Am. J. Respir. Crit. Care Med.; 2010; vol. 181; pp. 788-796.

Cryz, S.J. et al.; Immunotherapy and Vaccines; Ullmann's Encyclopedia of Industrial Chemistry; 2000; vol. 18; pp. 647-722.

Dermer, G.B. Another Anniversary for the War on Cancer. Bio/Technology, 1994, 12, 320.

Freshney, R.I., et al,, "Culture of Animal Cells." A Manual of Basic Technique, Alan R. Liss, Inc., 1983, New York, 1-7.

Flood-Page, P. et al.; A Study to Evaluate Safety and Efficacy of Mepolizumab in Patients with Moderate Persistent Asthma; Am. J. Respir. Crit. Care Med.; Dec. 1, 2007; vol. 176, No. 11; pp. 1062-1071.

Gautschi, O., et al. "Aurora Kinases as Anticancer Drug Targets." Clin Cancer Res., Mar. 15, 2008, 14(6), 1639-1648.

Gauvreau, G.M. et al.; Effects of Interleukin-13 Blockade on Allergen-induced Airway Responses in Mild Atopic Asthma; Am. J. Respir. Crit. Care Med.; Nov. 5, 2010; doi:1 0.1164/rccm.201 008-121 OOC.

Golub, T.R., et al. "Molecular Classification of Cancer: Class Discovery and Class Prediction by Gene Expression Monitoring." Science, Oct. 15, 1999, 286, 531-537.

Gould P.L.; Salt Selection for Basic Drugs; International Journal of Pharmaceutics; 1986; 33; 201-217.

Haldar, P., et al., Mepolizumab and Exacerbations of Refractory Eosinophilic Asthma; The New England Journal of Medicine; 2009; vol. 360(10); pp. 973-984.

Hirota, K., et al.; "Discovery of 8-Hydroxyadenines as a Novel Type of Interferon Inducer"; J. Med. Chem.; 2002; vol. 45, No. 25; pp. 5419-5422; American Chemical Society.

Huber, J.P et al.; Cutting Edge: Type I IFN Reverses Human Th2 Commitment and Stability by Suppressing GATA3; The Journal of Immunology; 2010; vol. 185; pp. 813-817.

Hussein, W.M., et al. Toll-like receptor agonists: a patent review (2011-2013); Expert Opinion on Therapeutic Patents, Jan. 24, 2014, pp. 1-18.

Isobe, Y., et al.; Synthesis and Biological Evaluation of Novel 9-Substituted-8-hydroxyadenine Derivatives as Potent Interferon Inducers; J. Med. Chem.; 2006; vol. 49, No. 6; pp. 2088-2095; American Chemical Society.

(56) References Cited

OTHER PUBLICATIONS

Kariyawasam, H.H., Et al.; Effects of Anti-IL-13 (Novartis QAX576) on Inflammatory Responses Following Nasal Allergen Challenge (NAC); Am. J. Respir. Crit. Care Med.; 2009; vol. 179; A3642.

Kurimoto, A., et al.; Prodrugs of 9-Benzyl-8-hydroxy-2-(2-hydroxyethylthio)adenine: Potent Interferon Inducing Agents in Monkeys; Chem. Pharm. Bull.; 2004; vol. 52, No. 4; pp. 466-469; Pharmaceutical Society of Japan.

Leaker, B.R., et al. The Effects of the Novel Toll-Like Receptor 7 (TLR7) Agonist AZD 8848 on Allergen-Induced Responses in Patients With Mild Asthma, Publication p. A4184.

Liu, Y-J., IPC: Profesional Type 1 Interferon-Producing Cells and Plasmacytoid Dendridic Cell Precursors, Ann. Rev. Immunol., 2005; 23:275-306.

Ma, R., Additive effects of CpG ODN and R-848 as adjuvants on augmenting immune responses to HBsAg vaccination, Biochem. Biophys., Res. Commun., 2007; 361:537-542.

McMahon G., et al. VEGF Receptor Signaling in Tumor Angiogenesis, The Oncologist, 2000, 5(Suppl1), pp. 3-10.

Mountzios, G., et al. "Aurora kinases as targets for cancer therapy." Cancer Treatment Reviews, 2008, 34, 175-182.

Pinedo, H.M., et al. Translational Research: The Role of VEGH in Tumor Angiogenesis, The Oncologist, 2000, 5 (Suppl1), pp. 1-2.

Pyne, S., et al. "Spingosine Kinase Inhibitors and Cancer: Seeking the Golden Sword of Hercules." Cancer Research, 2011, 71, 6576-6582.

Roemer, T., et al. "Auxiliary factors: a chink in the armor of MRSA resistance to β-lactam antibiotics." Current Opinion in Microbiology, 2013, 16, 538-548.

Simon, H-U., et al.; Clinical and immunological effects of low-dose IFN-α treatment in patients with corticosteroid-resistant asthma; Allergy; 2003; vol. 58; pp. 1250-1255.

Simone, J.V. Cecil Textbook of Medicine, edited by Bennet J.C. and Plum F., 20th edition, vol. 1, 1996, 1004-1010.

Snyder, J.W., et al. "Common bacteria whose susceptibility to antimicrobials is no longer predictable." J. Med. Liban, Pub Med Abstract, 2000, 48(4), 208-214.

Sugar, A.M., et al. "Comparison of Three Methods of Antifungal Susceptibility Testing with the Proposed NCCLS Standard Broth Microdilution Assay: Lack of Phenol Red," Diagno Microbiol Infect Dis, 1995, 21, 129-133.

Swarbrick, J., et al. Encyclopedia of Pharmaceutical Technology, Published 1996, vol. 13, pp. 453-499.

Tao, B., Treatment of allergic airway inflammation and hyper-responsiveness by imiquimod modulating transcription factors T-bet and GATA-3, Chin. Med. J. 2006; 119(8): 640-648.

Turner, W.W., et al. "Recent Advances in the Medicinal Chemistry of Antifungal Agents." Current Pharmaceutical Design, 1996, 2, 209-224.

Tsitoura, et al., *Clinical Pharm. & Therapetics*, 98(4):369-380 (2015).

* cited by examiner

Flow Diagram of the Manufacturing Process for Nasal Spray Solution of Compound (I), 100µg/mL Flow Diagram of the Manufacturing Process for Placebo Nasal Spray Solution Flow Diagram of the Manufacturing Process for Nasal Spray Solutions of Compound (I) 0.01μg/mL, 0.1μg/mL, and 1μg/mL Flow Diagram of the Filling and Assembly Process of Nasal Spray Solution of Compound (I)

COMPOSITION

This application is filed pursuant to 35 U.S.C. § 371 as a United States National Phase Application of International Patent Application No. PCT/EP2012/064139 filed Jul. 19, 2012, which claims priority from U.S. Provisional Application No. 61/510,624 filed on Jul. 22, 2011.

FIELD OF THE INVENTION

This invention is directed to pharmaceutical compositions, dosage forms, and dosing regimens, in particular to certain discrete and particular dosages of 6-amino-2-{[(1S)-1-methylbutyl]oxy}-9-[5-(1-piperidinyl)pentyl]-7,9-dihydro-8H-purin-8-one, which may be useful in the treatment of various disorders, for example the treatment of allergic diseases and other inflammatory conditions, for example allergic rhinitis and allergic asthma.

BACKGROUND OF THE INVENTION

International Patent Application, publication number WO 2010/018133 (SmithKline Beecham Corporation), relates to certain purine derivatives disclosed as inducers of human interferon which may be useful in the treatment of various disorders, for example the treatment of allergic diseases and other inflammatory conditions, for example allergic rhinitis and allergic asthma. One particular purine derivative disclosed in WO 2010/018133 is 6-amino-2-{[(1S)-1-methylbutyl]oxy}-9-[5-(1-piperidinyl)pentyl]-7,9-dihydro-8H-purin-8-one. Co-pending International Patent Application, application number PCT/EP2009/051830 (GlaxoSmithKline LLC), discloses a maleate salt of 6-amino-2-{[(1S)-1-methylbutyl]oxy}-9-[5-(1-piperidinyl)pentyl]-7,9-dihydro-8H-purin-8-one.

SUMMARY OF THE INVENTION

This invention is directed to pharmaceutical dosage forms, means for providing such pharmaceutical dosage forms, pharmaceutical compositions, and dosing regimens for 6-amino-2-{[(1S)-1-methylbutyl]oxy}-9-[5-(1-piperidinyl)pentyl]-7,9-dihydro-8H-purin-8-one ('Compound (I)')

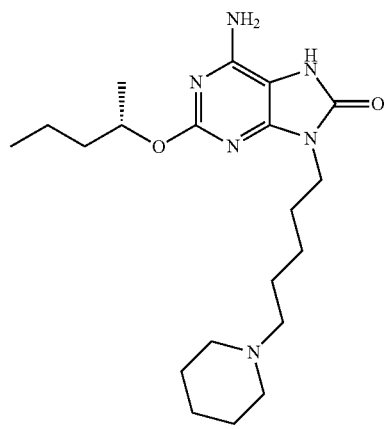

Compound (I)

which may be useful in the treatment of various disorders, for example the treatment of allergic diseases and other inflammatory conditions, for example allergic rhinitis and allergic asthma.

DETAILED DESCRIPTION OF THE INVENTION

Figure 1:
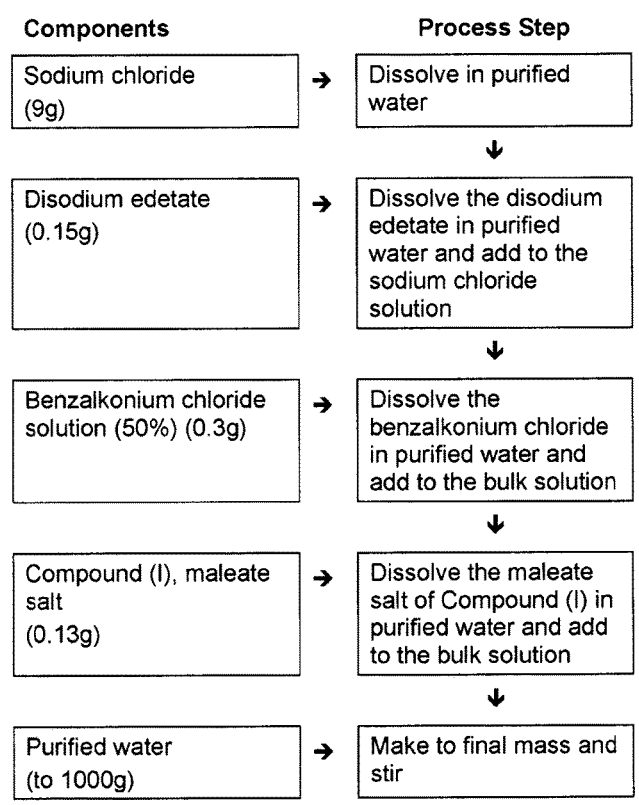
FIG. 1 shows a Flow Diagram of the Manufacturing Process for Nasal Spray Solution of Compound (I), 100 μg/mL.

International Patent Application, publication number WO 2010/018133 (SmithKline Beecham Corporation), relates to certain purine derivatives disclosed as inducers of human interferon which may be useful in the treatment of various disorders, for example the treatment of allergic diseases and other inflammatory conditions, for example allergic rhinitis and allergic asthma. One particular purine derivative disclosed in WO 2010/018133 is 6-amino-2-{[(1S)-1-methylbutyl]oxy}-9-[5-(1-piperidinyl)pentyl]-7,9-dihydro-8H-purin-8-one. Co-pending International Patent Application, application number PCT/EP2009/051830 (GlaxoSmithKline LLC), discloses a maleate salt of 6-amino-2-{[(1S)-1-methylbutyl]oxy}-9-[5-(1-piperidinyl)pentyl]-7,9-dihydro-8H-purin-8-one (hereinafter 'Compound (I)').

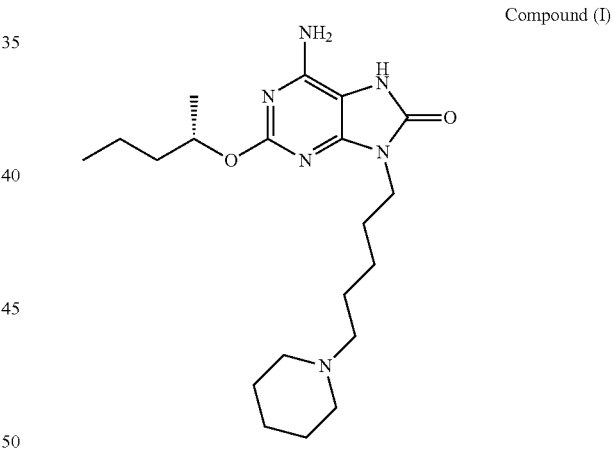

Compound (I)

It is now surprisingly indicated that certain discrete and particular dosages of Compound (I) may be useful in the treatment of various disorders, for example the treatment of allergic diseases and other inflammatory conditions, for example allergic rhinitis and allergic asthma. Accordingly, in a first aspect, there is provided a pharmaceutical dosage form comprising Compound (I), or a pharmaceutically acceptable salt thereof, and means for providing a metered-dose of Compound (I), or a pharmaceutically acceptable salt thereof.

A suitable pharmaceutical dosage form provides 0.5 nanogramme to 20000 nanogrammes of Compound (I) per actuation of the metering means, for example 0.5 nanogramme to 5 microgrammes, for example 1 nanogramme to 5 microgrammes, for example 0.5 nanogramme to 999 nanogrammes, for example 1 nanogramme to 999 nanogrammes.

In a further aspect, there is provided a pharmaceutical composition comprising Compound (I) or a pharmaceutically acceptable salt thereof, characterised in that the pharmaceutical composition is suitable for use with metering means.

In a further aspect, there is provided a method of treatment of allergic diseases and other inflammatory conditions, for example allergic rhinitis and allergic asthma, which method comprises the administration of Compound (I), or a pharmaceutically acceptable salt thereof, in an amount equivalent to 0.5 nanogramme to 40000 nanogrammes of Compound (I), for example 1 nanogramme to 20000 nanogrammes, for example 2 nanogrammes to 20000 nanogrammes, for example 1 nanogramme to 4000 nanogrammes, for example 2 nanogrammes to 4000 nanogrammes, for example 1 nanogramme to 999 nanogrammes, for example 2 nanogrammes to 999 nanogrammes, to a human in need thereof.

There is also provided Compound (I) or a pharmaceutically acceptable salt thereof, for use in treatment of allergic diseases and other inflammatory conditions, for example allergic rhinitis and allergic asthma, characterised in that 0.5 nanogramme to 40000 nanogrammes, for example 1 nanogramme to 20000 nanogrammes, for example 2 nanogrammes to 20000 nanogrammes, for example 1 nanogramme to 4000 nanogrammes, for example 2 nanogrammes to 4000 nanogrammes, for example 1 nanogramme to 999 nanogrammes, for example 2 nanogrammes to 999 nanogrammes, of Compound (I) is administered to a human in need thereof.

Examples of doses of Compound (I) are 0.5 nanogramme, 1 nanogramme, 2 nanogrammes, 5 nanogrammes, 10 nanogrammes, 20 nanogrammes, 30 nanogrammes, 40 nanogrammes, 50 nanogrammes, 60 nanogrammes, 70 nanogrammes, 80 nanogrammes, 90 nanogrammes, and 100 nanogrammes of Compound (I).

Compounds of formula (I) and pharmaceutically acceptable salts thereof may be administered at any appropriate frequency, for example 1-7 times per week, for example once per week.

A desired dose of Compound (I) may be provided by one or two actuations of the metering means as appropriate given the amount of the pharmaceutical composition dispensed per actuation of the metering means, and the concentration of the pharmaceutical composition being dispensed. For example, two actuations of the metering means may be used. Suitable pharmaceutically acceptable salts of Compound (I) include those described in WO 2010/018133 and a maleate salt. In one aspect, the pharmaceutically acceptable salt is a maleate salt, in particular the 1:1 maleate salt.

The pharmaceutical compositions comprising Compound (I), or a pharmaceutically acceptable salt thereof, are suitably administered by the intranasal or inhaled route.

Compositions and Dosage Forms

Compositions for intranasal administration include aqueous compositions administered to the nose by drops or by pressurised pump. Suitable compositions contain water as the diluent or carrier for this purpose. Compositions for administration to the lung or nose may contain one or more excipients, for example one or more suspending agents, one or more preservatives, one or more surfactants, one or more tonicity adjusting agents, one or more co-solvents, and may include components to control the pH of the composition, for example a buffer system. Further, the compositions may contain other excipients such as antioxidants, for example sodium metabisulphite, and taste-masking agents. Compositions may also be administered to the nose or other regions of the respiratory tract by nebulisation.

Intranasal compositions may permit the compound(s) of formula (I) or (a) pharmaceutically acceptable salt(s) thereof to be delivered to all areas of the nasal cavities (the target tissue) and further, may permit the compound(s) of formula (I) or (a) pharmaceutically acceptable salt(s) thereof to remain in contact with the target tissue for longer periods of time. A suitable dosing regimen for intranasal compositions would be for the patient to inhale slowly through the nose subsequent to the nasal cavity being cleared. During inhalation the composition would be administered to one nostril while the other is manually compressed. This procedure may be repeated for the other nostril.

The suspending agent(s), if included, will typically be present in an amount of from 0.1 to 5% (w/w), such as from 1.5% to 2.4% (w/w), based on the total weight of the composition. Examples of pharmaceutically acceptable suspending agents include, but are not limited to, Avicel® (microcrystalline cellulose and carboxymethylcellulose sodium), carboxymethylcellulose sodium, veegum, tragacanth, bentonite, methylcellulose, xanthan gum, carbopol and polyethylene glycols.

Compositions for administration to the lung or nose may contain one or more excipients may be protected from microbial or fungal contamination and growth by inclusion of one or more preservatives. Examples of pharmaceutically acceptable anti-microbial agents or preservatives include, but are not limited to, quaternary ammonium compounds (for example benzalkonium chloride, benzethonium chloride, cetrimide, cetylpyridinium chloride, lauralkonium chloride and myristyl picolinium chloride), mercurial agents (for example phenylmercuric nitrate, phenylmercuric acetate and thimerosal), alcoholic agents (for example chlorobutanol, phenylethyl alcohol and benzyl alcohol), antibacterial esters (for example esters of para-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives include, but are not limited to, sodium benzoate, sorbic acid, sodium propionate, methylparaben, ethylparaben, propylparaben and butylparaben. The preservative(s), if included, may be present in an amount of from 0.001 to 1% (w/w), such as from 0.015% to 0.5% (w/w) based on the total weight of the composition.

Compositions (for example wherein at least one compound is in suspension) may include one or more surfactants which functions to facilitate dissolution of the medicament particles in the aqueous phase of the composition. For example, the amount of surfactant used is an amount which will not cause foaming during mixing. Examples of pharmaceutically acceptable surfactants include fatty alcohols, esters and ethers, such as polyoxyethylene (20) sorbitan monooleate (Polysorbate 80), macrogol ethers, and poloxamers. The surfactant may be present in an amount of between about 0.01 to 10% (w/w), such as from 0.01 to 0.75% (w/w), for example about 0.5% (w/w), based on the total weight of the composition.

One or more tonicity-adjusting agent(s) may be included to achieve tonicity with body fluids e.g. fluids of the nasal cavity, resulting in reduced levels of irritancy. Examples of pharmaceutically acceptable tonicity-adjusting agents include, but are not limited to, sodium chloride, dextrose, xylitol, calcium chloride, glucose, glycerine and sorbitol. A tonicity-adjusting agent, if present, may be included in an amount of from 0.1 to 10% (w/w), such as from 4.5 to 5.5% (w/w), for example about 5.0% (w/w), based on the total weight of the composition.

The compositions of the invention may be buffered by the addition of suitable buffering agents such as sodium citrate, citric acid, trometamol, phosphates such as disodium phosphate (for example the dodecahydrate, heptahydrate, dihydrate and anhydrous forms), or sodium phosphate and mixtures thereof.

A buffering agent, if present, may be included in an amount of from 0.1 to 5% (w/w), for example 1 to 3% (w/w) based on the total weight of the composition.

Examples of taste-masking agents include sucralose, sucrose, saccharin or a salt thereof, fructose, dextrose, glycerol, corn syrup, aspartame, acesulfame-K, xylitol, sorbitol, erythritol, ammonium glycyrrhizinate, thaumatin, neotame, mannitol, menthol, eucalyptus oil, camphor, a natural flavouring agent, an artificial flavouring agent, and combinations thereof.

One or more co-solvent(s) may be included to aid solubility of the medicament compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400), and methanol. In one embodiment, the co-solvent is propylene glycol.

Co-solvent(s), if present, may be included in an amount of from 0.05 to 30% (w/w), such as from 1 to 25% (w/w), for example from 1 to 10% (w/w) based on the total weight of the composition.

Compositions for inhaled administration include aqueous, organic or aqueous/organic mixtures, dry powder or crystalline compositions administered to the respiratory tract by pressurised pump or inhaler, for example, reservoir dry powder inhalers, unit-dose dry powder inhalers, pre-metered multi-dose dry powder inhalers, nasal inhalers, nebulisers, or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulisation. Such compositions may be aqueous solutions or suspensions.

Compositions for administration topically to the nose or to the lung include aqueous compositions delivered to the nasal cavities by pressurised pump. Suitable compositions contain water as the diluent or carrier for this purpose. Aqueous compositions for administration to the lung or nose may be provided with conventional excipients such as buffering agents, tonicity-modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity. A fluid dispenser of the aforementioned type is described and illustrated in International Patent Application publication number WO 2005/044354 (Glaxo Group Limited). The dispenser has a housing which houses a fluid-discharge device having a compression pump mounted on a container for containing a fluid composition. The housing has at least one finger-operable side lever which is movable inwardly with respect to the housing to move the container upwardly in the housing by means of a cam to cause the pump to compress and pump a metered dose of the composition out of a pump stem through a nasal nozzle of the housing. In one embodiment, the fluid dispenser is of the general type illustrated in FIGS. 30-40 of WO 2005/044354.

Aqueous compositions containing a compound of formula (I) or a pharmaceutically acceptable salt thereof may also be delivered by a pump as disclosed in International Patent Application publication number WO 2007/138084 (Glaxo Group Limited), for example as disclosed with reference to FIGS. 22-46 thereof.

Dry powder compositions for topical delivery to the lung by inhalation may, for example, be presented in capsules and cartridges of for example gelatine, or blisters of for example laminated aluminium foil, for use in an inhaler or insufflator. Powder blend compositions generally contain a powder mix for inhalation of the compound of formula (I) or a pharmaceutically acceptable salt thereof and a suitable powder base (carrier/diluent/excipient substance) such as mono-, di-, or polysaccharides (for example lactose or starch). Dry powder compositions may also include, in addition to the drug and carrier, a further excipient (for example a ternary agent such as a sugar ester for example cellobiose octaacetate, calcium stearate, or magnesium stearate.

In one embodiment, a composition suitable for inhaled administration may be incorporated into a plurality of sealed dose containers provided on medicament pack(s) mounted inside a suitable inhalation device. The containers may be rupturable, peelable, or otherwise openable one-at-a-time and the doses of the dry powder composition administered by inhalation on a mouthpiece of the inhalation device, as known in the art. The medicament pack may take a number of different forms, for instance a disk-shape or an elongate strip.

Representative inhalation devices are the DISKHALER™ and DISKUS™ devices, marketed by GlaxoSmithKline.

A dry powder inhalable composition may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ (AstraZeneca), TWISTHALER™ (Schering) and CLICKHALER™ (Innovata.)

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ (GlaxoSmithKline) and HANDIHALER™ (Boehringer Ingelheim.)

For administration by the intranasal route, a suitable metering means is a pump providing a pre-set amount of the pharmaceutical dosage form per actuation, for example 50 microliters per actuation or 100 microliters per actuation.

A suitable pump is a Valois VP7 spray pump (Valois Pharm, Route des Falaises, 27100 Le Vaudreuil, France).

A suitable pharmaceutical composition for intranasal administration comprising Compound (I), or a pharmaceutically acceptable salt thereof, which is suitable for use with a metering means is a suspension or solution, for example an aqueous solution. The pharmaceutical composition may contain from 0.01 to 1000 microgrammes of Compound (I) per milliliter, for example 0.01 microgrammes to 100 microgrammes of Compound (I) per milliliter.

The pharmaceutical composition for intranasal administration comprising Compound (I), or a pharmaceutically acceptable salt thereof, suitable for use with a metering means, may be held in any container suitable for the containment and storage of the composition, which container is adapted to receive the metering means, for example a Type 1 amber glass bottle (available, for example, from Saint Gobain Desjonqueres (SGD), Avenue Pierre et Marie Curie, Mers-les-Bains, Picardie, France, 80350.)

For intranasal administration, the composition of the invention may be administered once per week, for example one actuation of the metering means to each nostril per week, for 6 weeks.

The components other than Compound (I), or a pharmaceutically acceptable salt thereof, used to prepare these compositions are commercially available, for example Sodium Chloride Ph. Eur. or USP (e.g. Morton Salt, 123 N. Wacker Drive, Chicago, Ill., 60606, US), Benzalkonium Chloride Solution Ph. Eur. or USP (e.g. Merck Chemicals LTD., Boulevard Industrial Park, Padge Road, Beeston, Nottingham NG9 2JR, UK), Disodium Edetate Ph. Eur. or USP (e.g. Dow Chemical Co, Seal Sands, Middlesbrough, Cleveland, TS2 1UD, UK).

For the avoidance of doubt, when reference is made herein to scalar amounts, including microgramme amounts, nanogramme amounts and % weight amounts, of 'Compound (I), or a pharmaceutically acceptable salt thereof, the scalar amount referred to is made in respect of Compound (I) per se. For example, 1.3 nanogrammes of Compound (I) in the form of the 1:1 maleate salt is that amount of maleate salt which contains 1 nanogramme of Compound (1).

Compound (I) exists in tautomeric forms. It will be understood that the present invention encompasses all of the tautomers of Compound (I) whether as individual tautomers or as mixtures thereof.

Compound (I) or a pharmaceutically acceptable salt thereof, may be prepared using known methods, for example those disclosed in WO 2010/018133.

A maleate salt of Compound (I) may be prepared from Compound (I) by reacting 6-amino-2-{[(1S)-1-methylbutyl]oxy}-9-[5-(1-piperidinyl)pentyl]-7,9-dihydro-8H-purin-8-one with maleic acid, in a suitable solvent to produce 6-amino-2-{[(1S)-1-methylbutyl]oxy}-9-[5-(1-piperidinyl)pentyl]-7,9-dihydro-8H-purin-8-one in the form of a maleate salt. In one aspect, the process produces a 1:1 ratio of maleic acid:6-amino-2-{[(1S)-1-methylbutyl]oxy}-9-[5-(1-piperidinyl)pentyl]-7,9-dihydro-8H-purin-8-one.

The pharmaceutical compositions of the invention may be prepared and formulated according to conventional methods such as those disclosed in the British, European, and United States Pharmacopoeias, Remington's Pharmaceutical Sciences (Mack Publishing Co.), Martindale The Extra Pharmacopoeia (London, The Pharmaceutical Press), and Harry's Cosmeticology (Leonard Hill Books).

Figure 2:
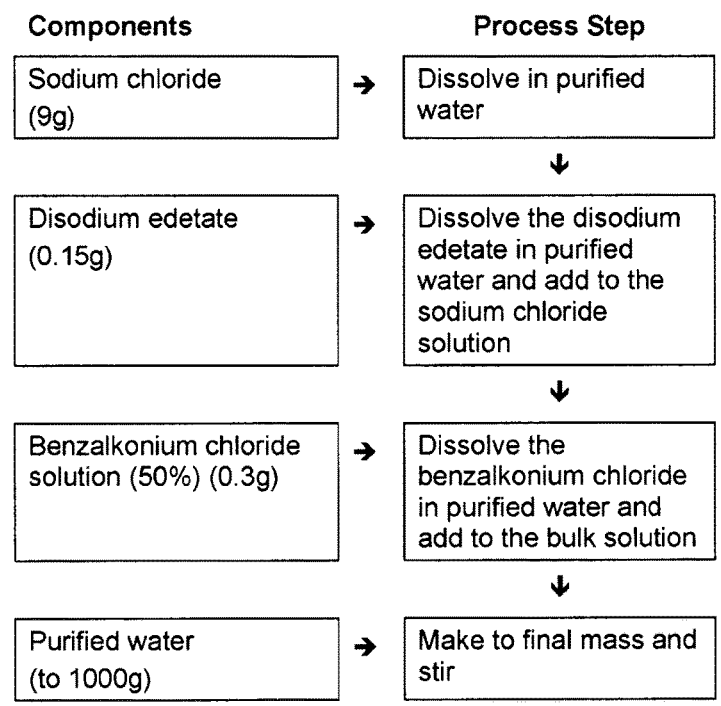
FIG. 2 shows a flow diagram of the Manufacturing Process for Placebo Nasal Spray Solution.
Figure 3:
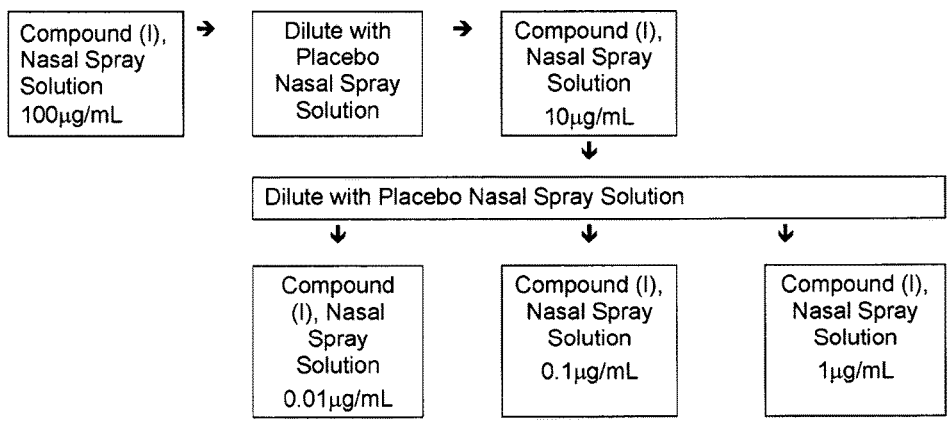
FIG. 3 shows a Flow Diagram of the Manufacturing Process for Nasal Spray Solutions of Compound (I) 0.01 μg/mL, 0.1 μg/mL, and 1 μg/mL.
Figure 4:
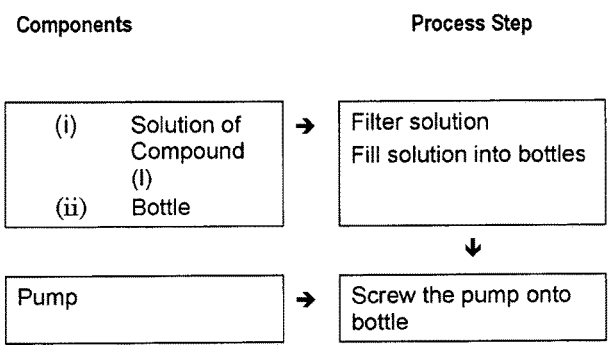
FIG. 4 shows a Flow Diagram of the Filing and Assembly Process of Nasal Spray Solution of Compound (I).

The pharmaceutical compositions for intranasal administration are typically prepared from a concentrated solution by serial dilution. The components of the formulation are dissolved in purified water and mixed to provide a concentrated solution of Compound (I) or a pharmaceutically acceptable salt thereof, for example 100 microgrammes per milliliter. A placebo solution is also prepared in a similar manner to the concentrated solution, but without Compound (I) or a pharmaceutically acceptable salt thereof. The concentrated solution is diluted with the placebo solution to provide formulations of the desired concentration. Examples of the preparation of solutions containing the maleate salt of Compound (I) and a placebo solution are provided in FIGS. 1-3.

Preparation of Compound (I), Maleate Salt

Reference Example 1: 6-Amino-2-{[(1S)-1-methylbutyl]oxy}-9-[5-(1-piperidinyl)pentyl]-7,9-dihydro-8H-purin-8-one, Maleate Salt

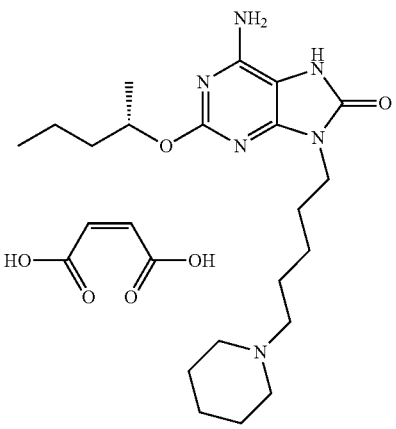 [SMILES: CCC[C@H](C)Oc1nc(N)c2[nH]c(=O)n(CCCCCN3CCCCC3)c2n1 ; O=C(O)/C=C\C(=O)O]

Preparation 1

6-Amino-2-{[(1 S)-1-methylbutyl]oxy}-9-[5-(1-piperidinyl)pentyl]-7,9-dihydro-8H-purin-8-one (for example, as prepared for Reference Example 1) (0.384 g, 0.98 mmol) was dissolved in isopropyl alcohol (4.6 mL, 12 vols) and heated to 40° C. Maleic acid (0.114 g, 0.98 mmol) was added. A clear solution was obtained. During cooling to room temperature, precipitation occurred. The slurry was filtered, washed with iso-propyl alcohol (5 mL) and dried under reduced pressure at 40° C. to constant weight. 6-Amino-2-{[(1S)-1-methylbutyl]oxy}-9-[5-(1-piperidinyl)pentyl]-7,9-dihydro-8H-purin-8-one, maleate salt (0.305 g, 61% th) was obtained as a white solid.

$^1$H NMR confirms a 1:1 ratio of maleic acid:6-amino-2-{[(1S)-1-methylbutyl]oxy}-9-[5-(1-piperidinyl) pentyl]-7, 9-dihydro-8H-purin-8-one. $^1$H NMR (400 MHz, DMSO-ds) δ ppm, 9.85 (1H, s, $(CH_2)_3NHCO$), 8.85 (1H, br s, $NH^+$), 6.39 (2H, s, $NH_2$), 6.02 (2H, s, $HO_2C(CH_2)$), 5.00 (1H, m, J=6.2 Hz, $CH_3CH$), 3.68 (2H, t, J=6.8, Hz $NCH_2$), 3.40 (2H, m, $NCH_2$), 2.98 (2H, m, J=8.1 Hz $NCH_2$), 2.82 (2H, br s, $NCH_2$), 1.85-1.24 (16H, m, 8×$CH_2$), 1.21 (3H, d, J=6.1 Hz, $CHCH_3$), 0.89 (3H, t, J=7.3 Hz, $CH_2CH_3$), 2.5 (solvent (DMSO)).

Preparation 2

A solution of 6-amino-2-{[(1S)-1-methylbutyl]oxy}-9-[5-(1-piperidinyl) pentyl]-7,9-dihydro-8H-purin-8-one (for example, as prepared for Reference Example 1) (1.46 g, 3.74 mmol) in iso-propyl alcohol (14.6 mL, 10 vols) was clarified (filtered at room temperature through a BondElut cartridge) and then heated to approximately 50° C. A solution of maleic acid (0.434 g, 3.74 mmol) in isopropyl alcohol (2.9 mL, 2 vols) was added. The resulting solution was then seeded and cooled to 45° C. Further seed was added. The resulting slurry was cooled to room temperature and held overnight (approximately 16 hours), then cooled in an ice/water bath for 30 minutes. The slurry was filtered, washing with iso-propyl alcohol (4.5 mL, 3 vols and then 3 mL, 2 vols). The product was dried under reduced pressure at 40° C. to constant weight to give 6-amino-2-{[(1S)-1-methylbutyl]oxy}-9-[5-(1-piperidinyl) pentyl]-7,9-dihydro-8H-purin-8-one, maleate salt (1.305 g, 69% th).

Reference Example 2: 6-Amino-2-{[(1S)-1-methylbutyl]oxy}-9-[5-(1-piperidinyl)pentyl]-7,9-dihydro-8H-purin-8-one, Maleate Salt A solution of 6-amino-2-{[(1S)-1-methylbutyl]oxy}-9-[5-(1-piperidinyl) pentyl]-7,9-dihydro-8H-purin-8-one (398 g, 1.02 mol) in iso-propyl alcohol (3.59 L, 10 vols) was clarified (filtered at room temperature through a 5 micron in-line filter) and then heated to 50° C. A solution of maleic acid (118 g, 1.02 mol) in iso-propyl alcohol (997 mL, 2 vols) was added. The resulting solution was then seeded (1.2 g, 3 mmol) and cooled to 40-45° C. and aged for 30 minutes. The resulting slurry was cooled to 10° C. over 1.5 hours, held for 30 minutes and then filtered, washing with iso propyl alcohol (1.20 L, 3 vols). The product was dried under reduced pressure at 40° C. to constant weight to give 6-amino-2-{[(1S)-1-methylbutyl]oxy}-9-[5-(1-piperidinyl) pentyl]-7,9-dihydro-8H-purin-8-one, maleate salt (296 g, 57% th).

The following examples illustrate the invention but do not limit it in any way.

EXAMPLES

Example 1: Composition of Nasal Spray Solution Containing Compound (I) at 0.01 µg/mL, 0.1 µg/mL and 1 µg/mL

| Quantity | Concentration | Active ingredient Compound (I)[2] | Other components | | | |
|---|---|---|---|---|---|---|
| | | | Sodium chloride | Benzalkonium Chloride[3] | Disodium Edetate | Purified Water |
| Per Bottle | 0.01 µg/mL Compound (I) | | | | | |
| | µg/mL | 0.013 | 9000 | 300 | 150 | To 100 |
| | % w/w | 0.0000013 | 0.90 | 0.03 | 0.015 | |
| Per spray[1] | | | | | | |
| (100 µL pump) | µg | 0.0013[4] | 900 | 30 | 15 | To 100 |
| Per Bottle | 0.1 µg/mL Compound (I) | | | | | |
| | µg/mL | 0.13 | 9000 | 300 | 150 | To 100 |
| | % w/w | 0.000013 | 0.90 | 0.03 | 0.015 | |
| Per spray[1] | | | | | | |
| (100 µL pump) | µg | 0.013[5] | 900 | 30 | 15 | To 100 |
| Per Bottle | 1 µg/mL Compound (I) | | | | | |
| | µg/mL | 1.3 | 9000 | 300 | 150 | To 100 |
| | % w/w | 0.00013 | 0.90 | 0.03 | 0.015 | |
| Per spray[1] | | | | | | |
| (50 µL pump) | µg | 0.065 | 450 | 15 | 7.5 | To 50 |
| (100 µL pump) | µg | 0.13[6] | 900 | 30 | 15 | To 100 |
| Function | | Active | Tonicity agent | Preservative | Preservative | Vehicle |
| Reference to Standard | | | USP or Ph. Eur. | USP or Ph. Eur. | USP or Ph. Eur. | USP or Ph. Eur. |

Note:
[1]Theoretical quantity per spray (ex-device)
[2]The quantity of Compound (I) may be adjusted to reflect the assigned purity of the input drug substance (Compound (I) as 1:1 maleate salt). Salt to base factor is 1.3
[3]Aqueous solution containing 50% benzalkonium chloride
[4]Equates to 1 ng Compound (I)
[5]Equates to 10 ng Compound (I)
[6]Equates to 100 ng Compound (I)

Example 2: Composition of Nasal Spray Solution Containing Compound (I) at 10 μg/mL

| Quantity | Concentration | Active ingredient Compound (I)[2] | Sodium chloride | Other components Benzalkonium Chloride[3] | Disodium Edetate | Purified Water |
|---|---|---|---|---|---|---|
| Per Bottle | 10 μg/mL Compound (I) | | | | | |
| | μg/mL | 13 | 9000 | 300 | 150 | To 100 |
| | % w/w | 0.0013 | 0.90 | 0.03 | 0.015 | |
| Per spray[1] | | | | | | |
| (50 μL pump) μg | | 0.65[4] | 450 | 15 | 7.5 | To 50 |
| (100 μL pump) μg | | 1.3[5] | 900 | 30 | 15 | To 100 |
| Function | | Active | Tonicity agent | Preservative | Preservative | Vehicle |
| Reference to Standard | | | USP or Ph. Eur. | USP or Ph. Eur. | USP or Ph. Eur. | USP or Ph. Eur. |

Note:

[1] Theoretical quantity per spray (ex-device)

[2] The quantity of Compound (I) may be adjusted to reflect the assigned purity of the input drug substance (Compound (I) as 1:1 maleate salt). Salt to base factor is 1.3

[3] Aqueous solution containing 50% benzalkonium chloride

[4] Equates to 500 ng Compound (I)

[5] Equates to 1000 ng Compound (I)

Example 3: Composition of Nasal Spray Solution Containing Compound (I) at 100 μg/mL

| Quantity | Concentration | Active ingredient Compound (I)[2] | Sodium chloride | Other components Benzalkonium Chloride[3] | Disodium Edetate | Purified Water |
|---|---|---|---|---|---|---|
| Per Bottle | 100 μg/mL Compound (I) | | | | | |
| | μg/mL | 130 | 9000 | 300 | 150 | To 100 |
| | % w/w | 0.013 | 0.90 | 0.03 | 0.015 | |
| Per spray[1] | | | | | | |
| (50 μL pump) μg | | 6.5[4] | 450 | 15 | 7.5 | To 50 |
| (100 μL pump) μg | | 13[5] | 900 | 30 | 15 | To 100 |
| Function | | Active | Tonicity agent | Preservative | Preservative | Vehicle |
| Reference to Standard | | | USP or Ph. Eur. | USP or Ph. Eur. | USP or Ph. Eur. | USP or Ph. Eur. |

Note:

[1] Theoretical quantity per spray (ex-device)

[2] The quantity of Compound (I) may be adjusted to reflect the assigned purity of the input drug substance (Compound (I) as 1:1 maleate salt). Salt to base factor is 1.3

[3] Aqueous solution containing 50% benzalkonium chloride

[4] Equates to 5000 ng Compound (I)

[5] Equates to 10000 ng Compound (I)

The invention claimed is:
1. A pharmaceutical dosage form comprising Compound (I):

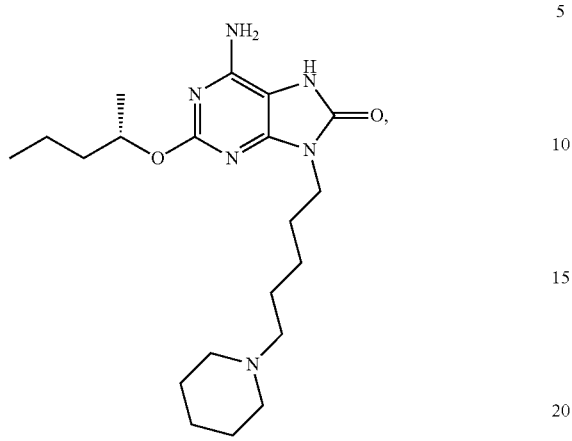

or a pharmaceutically acceptable salt thereof, and means for providing a metered-dose of Compound (I), or a pharmaceutically acceptable salt thereof, which provides about 10 nanogrammes of Compound (I) per actuation of the metering means.

2. A pharmaceutical dosage form according to claim 1, wherein the means is selected from the group consisting of a fluid dispenser with a pump mechanism and an inhalation device.

* * * * *